US012622729B2

(12) United States Patent
Kim

(10) Patent No.: US 12,622,729 B2
(45) Date of Patent: May 12, 2026

(54) CERVICAL PLATE FOR REOPERATION

(71) Applicant: SURGIOGEN CO., LTD., Daegu (KR)

(72) Inventor: Hwaseon Kim, Yongin-si (KR)

(73) Assignee: SURGIOGEN CO., LTD., Daegu (KR)

( * ) Notice: Subject to any disclaimer, the term of this patent is extended or adjusted under 35 U.S.C. 154(b) by 108 days.

(21) Appl. No.: 18/393,037

(22) Filed: Dec. 21, 2023

(65) Prior Publication Data

US 2024/0390041 A1 Nov. 28, 2024

(30) Foreign Application Priority Data

May 23, 2023 (KR) ........................ 10-2023-0066158

(51) Int. Cl.
*A61B 17/80* (2006.01)
*A61B 17/70* (2006.01)
*A61B 17/00* (2006.01)

(52) U.S. Cl.
CPC ...... *A61B 17/7059* (2013.01); *A61B 17/8057* (2013.01); *A61B 2017/00477* (2013.01)

(58) Field of Classification Search
CPC . A61B 17/80; A61B 17/8023; A61B 17/8033; A61B 17/8042; A61B 17/8057; A61B 17/8061; A61B 17/7059
See application file for complete search history.

(56) References Cited

U.S. PATENT DOCUMENTS

| | | | | |
|---|---|---|---|---|
| 6,139,550 A | * | 10/2000 | Michelson | A61B 17/80 |
| | | | | 606/295 |
| 6,306,139 B1 | * | 10/2001 | Fuentes | A61B 17/8042 |
| | | | | 606/295 |
| 9,044,275 B2 | * | 6/2015 | Weiman | A61B 17/8023 |
| 2009/0163960 A1 | | 6/2009 | Binder et al. | |
| 2012/0022600 A1 | | 1/2012 | Overes et al. | |
| 2015/0289908 A1 | * | 10/2015 | Stern | A61B 17/7059 |
| | | | | 606/289 |
| 2019/0046245 A1 | | 2/2019 | Ha et al. | |
| 2020/0360060 A1 | * | 11/2020 | Wuk | A61B 17/7059 |
| 2023/0225769 A1 | * | 7/2023 | James | A61B 17/7059 |
| | | | | 606/289 |

FOREIGN PATENT DOCUMENTS

| | | | |
|---|---|---|---|
| JP | H11-299804 A | 11/1999 |
| JP | 2007-515257 A | 6/2007 |
| JP | 2008-086817 A | 4/2008 |
| JP | 2019-030621 A | 2/2019 |
| JP | 2020-011090 A | 1/2020 |

(Continued)

*Primary Examiner* — Si Ming Ku
(74) *Attorney, Agent, or Firm* — Bridgeway IP Law Group, PLLC; Sang Ho Lee; Hyun Woo Shin

(57) ABSTRACT

A cervical plate for easy reoperation includes: a main plate of a rectangular panel shape, which is installed using a screw on the vertebra from which the disk has been removed during spinal operation to support and fix the surgical site vertebra; and a subsidiary plate of a panel shape, which is installed using a screw during reoperation on an adjacent area to the surgical site where the main plate is installed to support and fix the reoperation site vertebra, wherein the main plate and the subsidiary plate can be connected continuously, thereby allowing additional installation of the subsidiary plate while maintaining the installed state of the main plate.

9 Claims, 10 Drawing Sheets

(56)　　　　　References Cited

FOREIGN PATENT DOCUMENTS

| KR | 10-2013-0004669 | A | 1/2013 |
| KR | 10-2013-0057010 | A | 5/2013 |
| KR | 20-2014-0001295 | U | 3/2014 |
| KR | 10-1720142 | B1 | 3/2017 |
| KR | 10-2018-0062991 | A | 6/2018 |

* cited by examiner

CERVICAL PLATE FOR REOPERATION

CROSS-REFERENCE TO RELATED APPLICATION(S)

The present application claims benefit and priority to Korean patent application No. 10-2023-0066158 filed on May 23, 2023, in the Korean Intellectual Property Office, the entire disclosure of which is hereby incorporated by reference.

BACKGROUND OF THE INVENTION

Field of the Invention

The present disclosure relates to a cervical plate for easy reoperation, and more specifically, to a cervical plate for easy reoperation, in which a reoperation plate can be easily installed without the need to remove a previously installed plate during spinal reoperation.

Background Art

A vertebral body consists of 32 to 35 vertebrae forming the trunk and intervertebral disks located between the vertebrae, and is the core of a human body, which forms a support for the torso and connects the skull at the top and the pelvis at the bottom.

The vertebrae are composed of seven cervical vertebrae, twelve thoracic vertebrae, five lumbar vertebrae, five sacral vertebrae, and three to five coccygeal vertebrae from the top. In adults, the five sacral vertebrae fuse to form one sacrum, and the three to five coccygeal vertebrae fuse to form one coccyx.

In general, the cervical vertebrae are located at the uppermost position of the vertebral body and includes seven vertebrae. From the top, the first cervical vertebra is also called the atlas, and has a round shape with the articular surface supporting the skull, but lacks a vertebral centrum and a spinous process. The second cervical vertebra is also known as the axis, assists in the rotation of the neck, and has a spinous process that extends upward from the vertebral centrum. Each of the third to sixth cervical vertebrae has a small and wide vertebral centrum, a triangular vertebral foramen, and a bifurcated spinous processes. The seventh cervical vertebra is also known as the vertebra prominens, and has a long and non-bifurcated spinous process.

The cervical vertebrae with such structures and functions may be damaged or deformed due to external impacts from accidents or prolonged twisted postures. To fix the damaged or deformed cervical vertebrae, a procedure of inserting and fixing a cervical plate (cervical fixation device), including a plate and a screw, onto the cervical vertebrae is performed.

However, the conventional cervical plate has a disadvantage in that due to a wide fixation range, when reoperation is performed on an adjacent area, there is insufficient space to fasten a new screw. So, it is necessary to install a new screw after removing the existing cervical plate.

For example, if a patient who has undergone operation on the fourth and fifth cervical vertebrae has a problem at the fifth and sixth cervical vertebrae and needs reoperation, the operation on the fifth and sixth cervical vertebrae can only be performed after completely removing all of the existing cervical plates due to the insufficient space on the fifth cervical vertebra.

So, the conventional cervical plate has several problems of cumbersome operation, long operation time, and increased mental, physical, and financial burdens on the patient.

Therefore, there is a need for a method to solve the above problems.

SUMMARY OF THE INVENTION

Accordingly, the present disclosure has been made to solve the above-mentioned problems occurring in the prior arts, and it is an objective of the present disclosure to provide a cervical plate for easy reoperation, which includes a fitting groove formed at an end of a plate used in initial operation, and a protrusion protrudingly formed at an end of a plate used for reoperation, thereby allowing for smooth operation during reoperation without the need to remove the existing plate.

The objectives of the present disclosure are not limited to those mentioned above, and other objectives not mentioned herein will be clearly understood by those skilled in the art from the following description.

To accomplish the above object, according to the present disclosure, there is provided a cervical plate for reoperation including: a main plate having a rectangular panel shape, and configured to be installed using one or more screws on a surgical site of a vertebra to support and fix the vertebra; and a subsidiary plate having a panel shape and configured to be installed using one or more screws on a reoperation site located in an adjacent area to the surgical site where the main plate is installed to support and fix the vertebra, and the main plate and the subsidiary plate are continuously connected when installed, and the subsidiary plate is installed while maintaining an installed state of the main plate.

Moreover, the main plate and the subsidiary plate respectively include: a plurality of fastening holes, each of which have threads formed on an inner surface thereof to allow the one or more screws to penetrate in a screw manner and to be coupled to the vertebra.

In this instance, the plurality of fastening holes formed in the main plate are formed in sets of two, and multiple sets of the fastening holes are spaced at regular intervals in a length direction of the main plate.

Furthermore, the main plate further includes: a first cover unit rotatably coupled on an upper surface of the main plate via a coupling shaft, and the first cover unit selectively covers upper portions of one or more sets of the fastening holes formed in the main plate.

In this instance, the first cover unit is formed in a 'A' shape extending in two directions from the coupling shaft, and is provided in a same number as the sets of fastening holes formed in the main plate, and each of the first cover unit simultaneously opens or covers the upper portions of one set of the fastening holes formed in the main plate.

Additionally, the plurality of fastening holes formed in the subsidiary plate are formed around a periphery of the subsidiary plate in three directions based on a center of the subsidiary plate.

In this instance, the subsidiary plate further includes: a second cover unit rotatably coupled on an upper surface of the subsidiary plate via a coupling shaft, and the second cover unit selectively covers upper portions of the fastening holes formed in the subsidiary plate.

In this instance, the second cover unit is coupled to the center of the subsidiary plate, and is formed to extend in three directions from the coupling shaft, and the second cover unit simultaneously opens or covers the upper portions of the fastening holes formed in the subsidiary plate.

In addition, the main plate includes at least one observation hole, which is formed to vertically penetrate the main plate, and is located at a lower portion of the main plate during operation, thereby allowing visual confirmation of a vertebral surface contacting with the main plate.

In this instance, the main plate further includes a fitting groove formed on a surface to which the subsidiary plate is connected, to allow one side of the subsidiary plate to fit into the main plate, and the fitting groove is formed on two surfaces of the main plate, which are opposite to each other.

Moreover, the subsidiary plate includes a protrusion, which is configured to fit into the fitting groove of the main plate.

In this instance, the fitting groove includes a coupling groove, which is formed to be recessed inward.

Furthermore, the protrusion has a tapered shape that narrows towards a distal end thereof to be inserted into the coupling groove.

Additionally, the protrusion includes a coupling protrusion, which is formed to protrude outward and to be inserted and coupled into the coupling groove.

In this instance, the fitting groove has an upper portion and a lower portion, and the lower portion is recessed further inward in a horizontal direction such that the upper portion and the lower portion are differentiated to form multiple stages, the protrusion has an upper portion and a lower portion, and the lower portion protrudes further outward in the horizontal direction such that the upper portion and the lower portion are differentiated to form multiple stages, and the upper portion and the lower portion of the fitting groove and the upper portion and the lower portion of the protrusion respectively engage and complementarily couple to each other to enhance a coupling force between the main plate and the subsidiary plate.

In addition, the fitting groove has a tapered shape having an inclined surface, the protrusion has a tapered shape having an inclined surface which complementarily connects to the inclined surface of the fitting groove, and the fitting groove and the protrusion engage and complementarily couple to each other to enhance a coupling force between the main plate and the subsidiary plate.

The cervical plate for easy reoperation according to an embodiment of the present disclosure has the following effects.

First, the cervical plate for easy reoperation allows the installation of a subsidiary plate for reoperation without the need to remove the existing main plate.

Second, as a result, the cervical plate for easy reoperation can shorten the operation time and minimize physical, mental, and financial burdens on a patient.

The advantages of the present disclosure are not limited to the above-mentioned advantages, and other advantages, which are not specifically mentioned herein, will be clearly understood by those skilled in the art from the following description.

DETAILED DESCRIPTION OF THE PREFERRED EMBODIMENT

Figure 1:
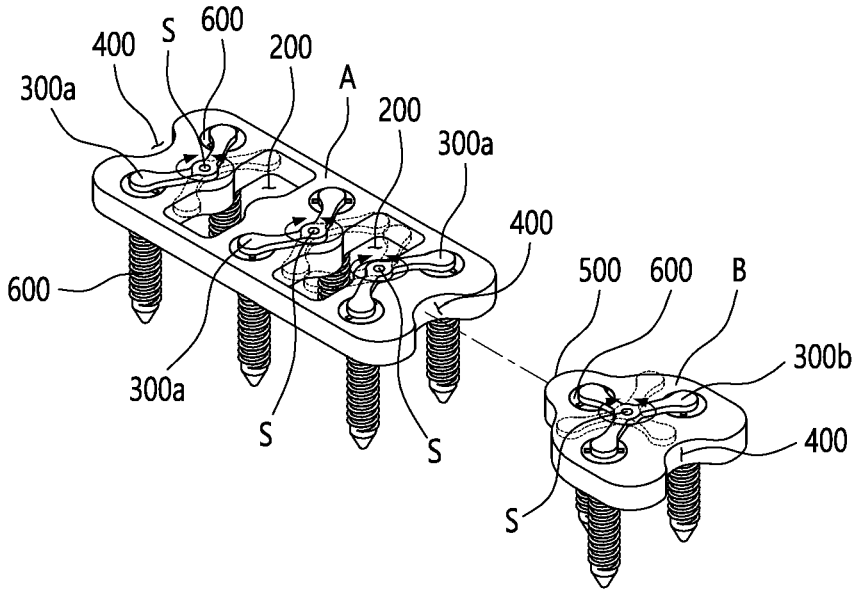
FIGS. 1 and 2 are illustrative views illustrating a structure of a cervical plate for easy reoperation according to a first embodiment of the present disclosure.

Hereinafter, preferred embodiments of the present disclosure will be described in detail with reference to the accompanying drawings. In describing the present embodiments, the same reference numerals and names are used for the same components, and a detailed description thereof will be omitted.

The present disclosure relates to a cervical plate for easy reoperation, and more specifically, to a cervical plate for easy reoperation, in which a reoperation plate can be easily installed without the need to remove a previously installed plate during spinal reoperation.

Since the conventional cervical plate used for spinal operation has a wide fixation range, when reoperation is required in an area adjacent to the existing surgical site, a sufficient space to couple a screw for fixing the cervical plate to be installed during reoperation cannot be secured. Accordingly, the conventional cervical plate has inconvenience to dismantle and reinstall all of the already installed cervical plates. Therefore, to overcome the inconvenience, the present disclosure proposes a cervical plate used for spinal operation, which minimize the mental, physical, and financial burdens on a patient.

For this purpose, in the present disclosure, the cervical plate used for the initial operation and the cervical plate used for reoperation can be configured as a set, and the cervical plate for reoperation can be installed in a sliding manner to be contiguous to the already installed cervical plate without dismantling the existing cervical plate. Therefore, the cervical plate for reoperation of the present disclosure can ensure convenience in operation, significantly reduce operation time, and minimize the mental, physical, and financial burdens on the patient.

Figure 2:
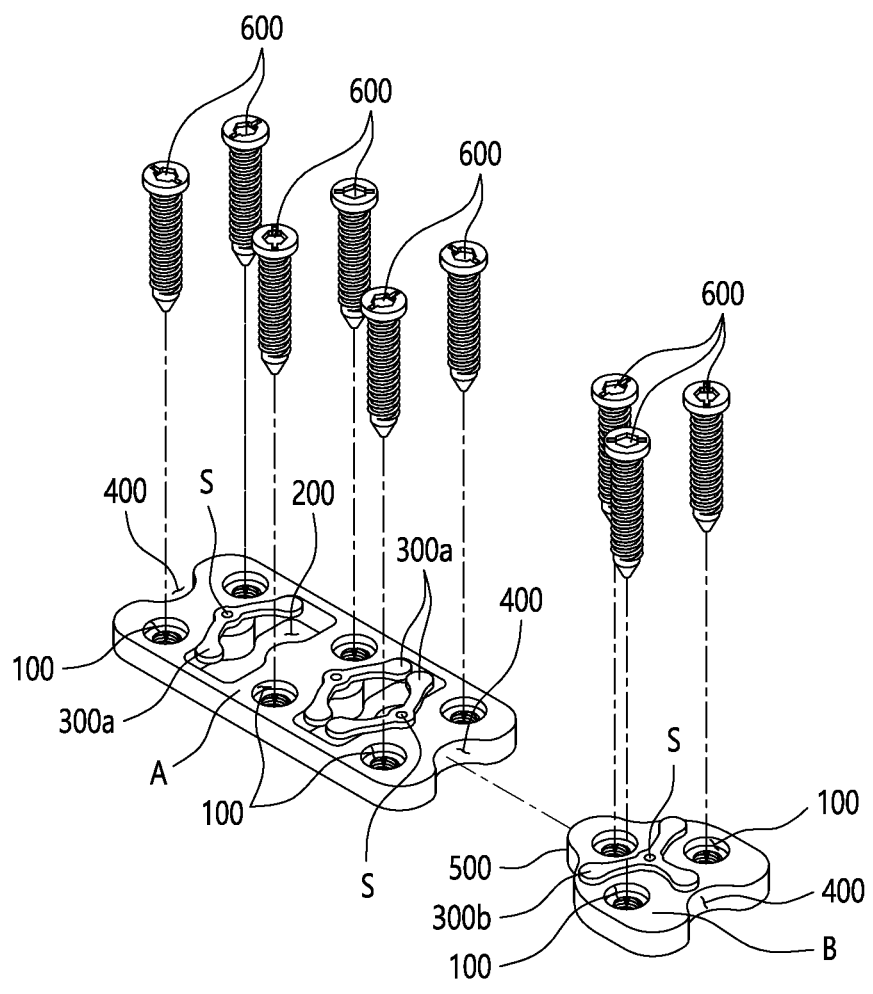

As illustrated in FIGS. 1 and 2, the cervical plate for easy reoperation according to the present disclosure may include: a square plate-shaped main plate A which is configured to support and fix the vertebra at a surgical site by being installed on the vertebra from which the disc has been removed during the initial spinal operation using screws 600; and a plate-shaped subsidiary plate B which, when reoperation is required in an area adjacent to the surgical site in which the main plate A is installed, is installed on the vertebra of the relevant area by a screw 600 to support and fix the vertebra of the reoperation site.

As described above, the main plate A refers to the cervical plate installed during the initial progress of spinal operation, and the subsidiary plate B can be understood as referring to the cervical plate installed when reoperation is conducted adjacent to the site of the initial operation.

In the case of the main plate A and the subsidiary plate B, when reoperation is conducted in the state in which the main plate A has been installed already, the subsidiary plate B can be installed without the need to dismantle the main plate A. For this purpose, the subsidiary plate B may have a connectable structure to be continued to the main plate A installed previously via a sliding method.

During surgical operation, the screw 600 can be fastened to the vertebra at the surgical site by passing through the main plate A and the subsidiary plate B. For this purpose, the main plate A and the subsidiary plate B can respectively include a plurality of fastening holes 100 which are formed in the inner surfaces thereof and respectively have threads in mesh with a thread of the screw 600 so that the screw 600 can pass through and can be coupled to the main plate A and the subsidiary plate B in a screw-like manner.

At this time, the fastening holes 100 formed in the main plate A are arranged in two rows in the length direction of the main plate A, that is, form a set of two. As described above, multiple sets of the two adjacent fastening holes 100 can be formed in the length direction of the main plate A.

It is preferable that the sets of fastening holes 100 formed in the length direction of the main plate A are spaced apart at regular intervals from each other to evenly and stably exert fixation to the vertebra when the main plate A is installed on the vertebra by the screw 600.

Furthermore, the main plate A can additionally include first cover units 300a to selectively cover the tops of the fastening holes 100, thereby preventing the indiscriminate separation of the screws 600 coupled through the fastening holes 100.

The first cover units 300a can be structured to rotate based on a coupling shaft S coupled to the upper surface of the main plate A. In this instance, the first cover units 300a can be provided on the upper surface of the main plate A in the same number as the fastening holes 100, such that one first cover unit 300a corresponds to one fastening hole 100, but the present disclosure is not limited thereto. For simplicity in the structure of the main plate A and ease of preventing the separation of the screws 600 coupled through the fastening holes 100 during surgical operation, it is preferable that the first cover unit 300a is structured to simultaneously open or cover the fastening holes 100 in the unit of sets in which two fastening holes 100 form a set.

In this instance, the rotational structure mentioned above can be understood as a coupling structure achieved by a rotational shaft member like a hinge, such that the first cover unit 300a is coupled to the main plate A.

For example, the first cover unit 300a can be coupled to the upper surface of the main plate A, specifically between the two fastening holes 100 that form a set, and be shaped like a 'Λ' extending on both sides about the coupling shaft S. This 'Λ'-shaped first cover unit 300a can simultaneously open or cover the tops of the sets of fastening holes 100 formed on the main plate A as it rotates.

For this purpose, the first cover units 300a can be provided in the same number as the sets of fastening holes 100 formed on the main plate A. For instance, assuming there are a total of six fastening holes 100 formed on the main plate A, the fastening holes are formed on the same line in pairs, each forming a set, so three sets of the fastening holes 100 can be formed. Therefore, three first cover units 300a can be coupled adjacent to each set on the upper surface of the main plate A.

In this state, the first cover unit 300a, which is formed in a 'Λ' shape, rotates about the portion coupled to the main plate A, such that one first cover unit 300a can simultaneously open or cover the tops of the two fastening holes 100 that form a set.

As described above, when the first cover unit 300a opens the fastening holes 100, the screw 600 penetrates and couples with the fastening holes 100. After the screw 600 is coupled, the first cover unit 300a is rotated so that the end of the first cover unit 300a covers the top of the fastening hole 100 to which the screw 600 is coupled, thereby preventing indiscriminate separation of the screw 600.

According to an embodiment of the present disclosure, the fastening holes 100 formed in the subsidiary plate B, which can be installed continuously with the main plate A, can be respectively formed on the periphery in three directions based on the center of the subsidiary plate B.

At this time, the subsidiary plate B is also installed on the vertebra of the surgical site by the screw 600 in the same manner as the main plate A. In order to prevent indiscriminate detachment of the screws 600 penetrating and coupling with the fastening holes 100 of the subsidiary plate B, a second cover unit 300b which selectively opens and closes the tops of the fastening holes 100 formed in the subsidiary plate B can be provided with a rotatable structure on the upper surface of the subsidiary plate B.

Here, the rotatable structure of the second cover unit 300b coupled to the subsidiary plate B can be made in the same manner as the structure of the first cover unit 300a coupled to the main plate A.

The second cover unit 300b can be coupled to the center of the subsidiary plate B, and is formed in a 'Y' shape extending in three directions about a coupling shaft S, such that the tops of the three fastening holes 100 formed respectively on the periphery in three directions based on the center of the subsidiary plate B can be opened or covered simultaneously. That is, each end of the 'Y' shaped second cover unit 300b can be coupled by a hinge-like rotational shaft at the center of the subsidiary plate B, and by rotating based on this coupled axis, the tops of the three fastening holes 100 formed in the subsidiary plate B can be simultaneously covered, thereby preventing indiscriminate separation of the screws 600 penetrating and coupling with the fastening holes 100. Alternatively, each end of the 'Y' shaped second cover unit 300b can be positioned between each of the three fastening holes 100 by rotation, thereby opening the tops of the three fastening holes 100 to allow the screws 600 to penetrate and couple.

According to an embodiment of the present disclosure, the main plate A may further include at least one observation hole 200 which penetrates through the upper and lower surfaces.

The observation hole 200 is positioned at the lower portion of the main plate A during surgical operation so that a surgeon can visually confirm in real-time the spinal surface which comes in contact with the main plate A, thereby ensuring the installation of the main plate A at an accurate position.

In addition, since at least one observation hole 200 is formed in the main plate A, the self-weight of the main plate A is reduced, thereby minimizing the burden on the patient's body, particularly on the vertebra after surgical operation.

As described above, the forms of the fastening holes 100 and the first cover unit 300a, which are formed in the main plate A, and the fastening hole 100 and the second cover units 300b, which are formed in the subsidiary plate B, and the mutual correspondence relationship according to the through coupling of the screw 600 can be more easily understood by referring to FIGS. 1 and 2.

According to an embodiment of the present disclosure, the main plate A installed through an initial operation, and the subsidiary plate B, which is newly installed through reoperation in an adjacent area after the initial operation to be continuously connected with the main plate A, may respectively have coupling parts with a mutually corresponding structure to facilitate the continuous connection.

For example, the main plate A which has been installed may have a fitting groove 400 formed on the side of the main plate A to which the subsidiary plate B is connected so that one side of the subsidiary plate B can be fit to slide. Since the subsidiary plate B can be connected to both sides of the main plate A in the length direction of the vertebra, it is preferable that the fitting groove 400 is formed on two opposite sides, which are symmetrical to each other, among the four sides of the main plate A.

Furthermore, the subsidiary plate B is installed on one side of the main plate A to be continuously connected to the main plate A. The subsidiary plate B may have a protrusion 500 formed at the front end thereof to correspond to and fit into the fitting groove 400 formed on the main plate A.

At this time, a fitting groove 400, identical to the above-mentioned fitting groove 400 formed on the main plate A, can be formed on the opposite side of the subsidiary plate B where the protrusion 500 is formed, so that additional connection of another subsidiary plate B can be made later.

For example, after the main plate A is installed in the first operation (meaning the initial operation), the subsidiary plate B can be installed to be continuously connected to the previously installed main plate A in the second operation (reoperation). If a third operation is performed later, the subsidiary plate B installed in the second operation and another subsidiary plate B can be continuously connected and installed. For this purpose, a protrusion 500 fitting into the fitting groove 400, and a fitting groove 400 for fitting a protrusion 500 formed on another subsidiary plate B may be respectively formed on opposite sides of the subsidiary plate B.

Figure 3A:
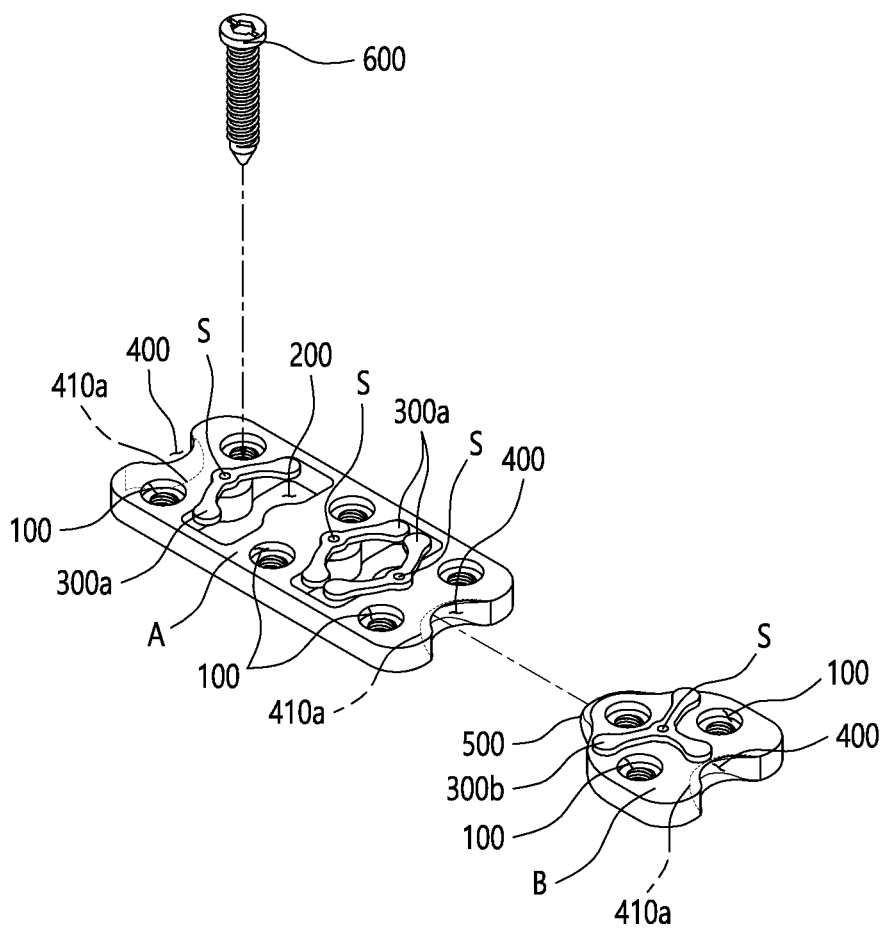
FIGS. 3A and 3B are illustrative views showing a coupling structure of a coupling groove and a protrusion in the cervical plate for easy reoperation according to the first embodiment of the present disclosure.
Figure 3B:
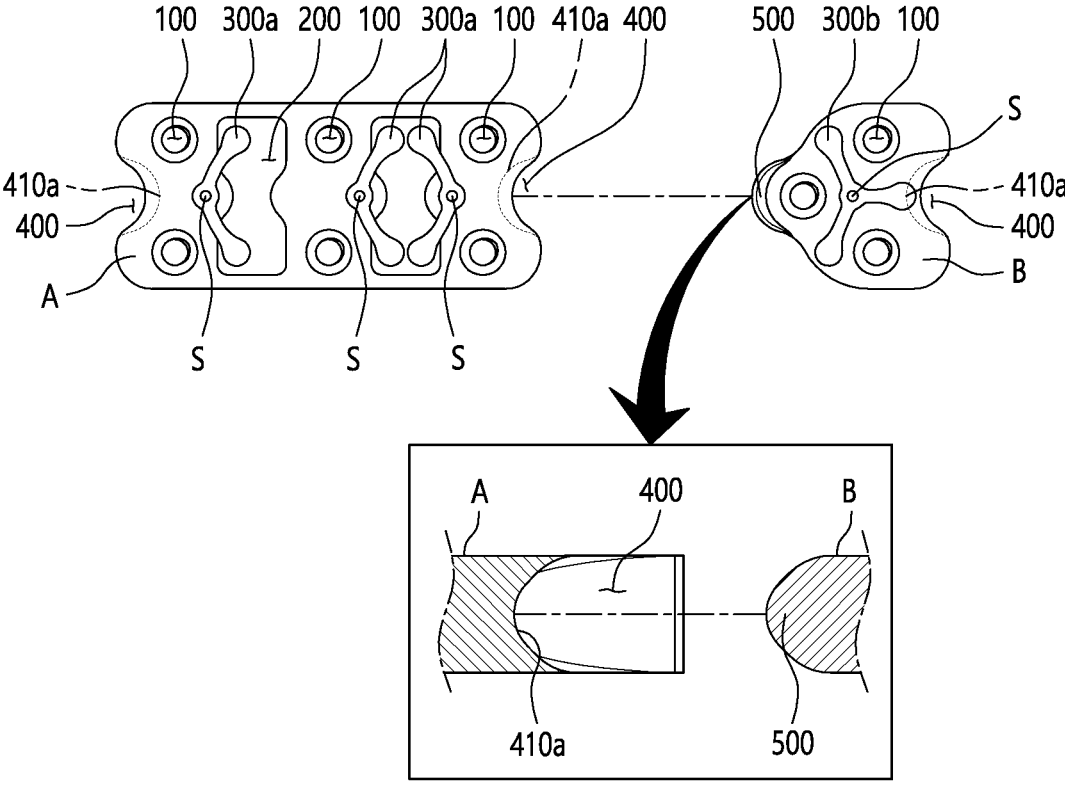

In this instance, as illustrated in FIGS. 3A and 3B, the fitting groove 400 may have a coupling groove 410a which has a horizontal direction and of which the inner circumferential surface is inwardly recessed. The protrusion 500 to be fitted into the fitting groove 400 may be formed in a taper shape such that a longitudinal-section area decreases towards the outside, so that it can be inserted into the coupling groove 410a formed in the fitting groove 400 in the horizontal direction.

As described above, the main plate A and the subsidiary plate B can enhance their coupling force through the interaction between the coupling groove 410a formed in the horizontal direction in the fitting groove 400 and the protrusion 500 formed in the taper shape with the longitudinal section area decreasing towards the outside, thereby preventing the main plate A and the subsidiary plate B from being indiscriminately separated from the installation position due to the patient's movement or external pressure after reoperation.

In this instance, as described above, the coupling groove 410a is formed by the inner circumferential surface of the fitting groove 400 bent horizontally, but it is not limited to having the same taper shape as the taper shape of the protrusion 500 inserted into the coupling groove 410a. As occasion demands, the fitting groove 400 may be formed in a vertical direction, not in a horizontal direction, to enable slidable coupling of the main plate A and the subsidiary plate B in the vertical direction.

Figure 6A:
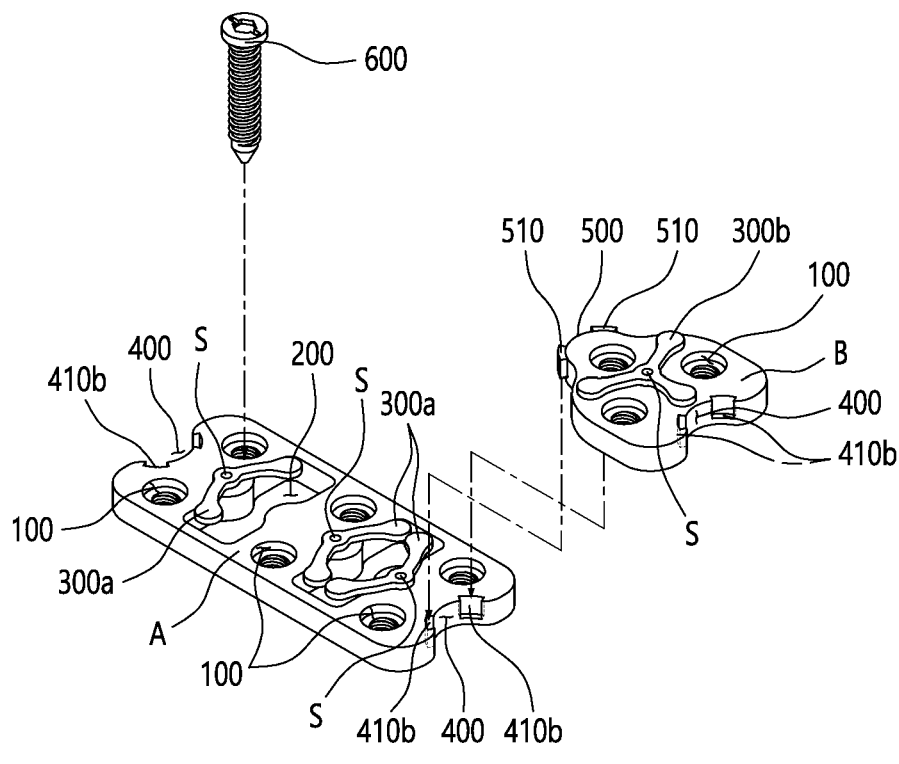
FIGS. 6A and 6B are illustrative views showing a coupling structure of a coupling groove and a protrusion in the cervical plate for easy reoperation according to the second embodiment of the present disclosure.
Figure 6B:
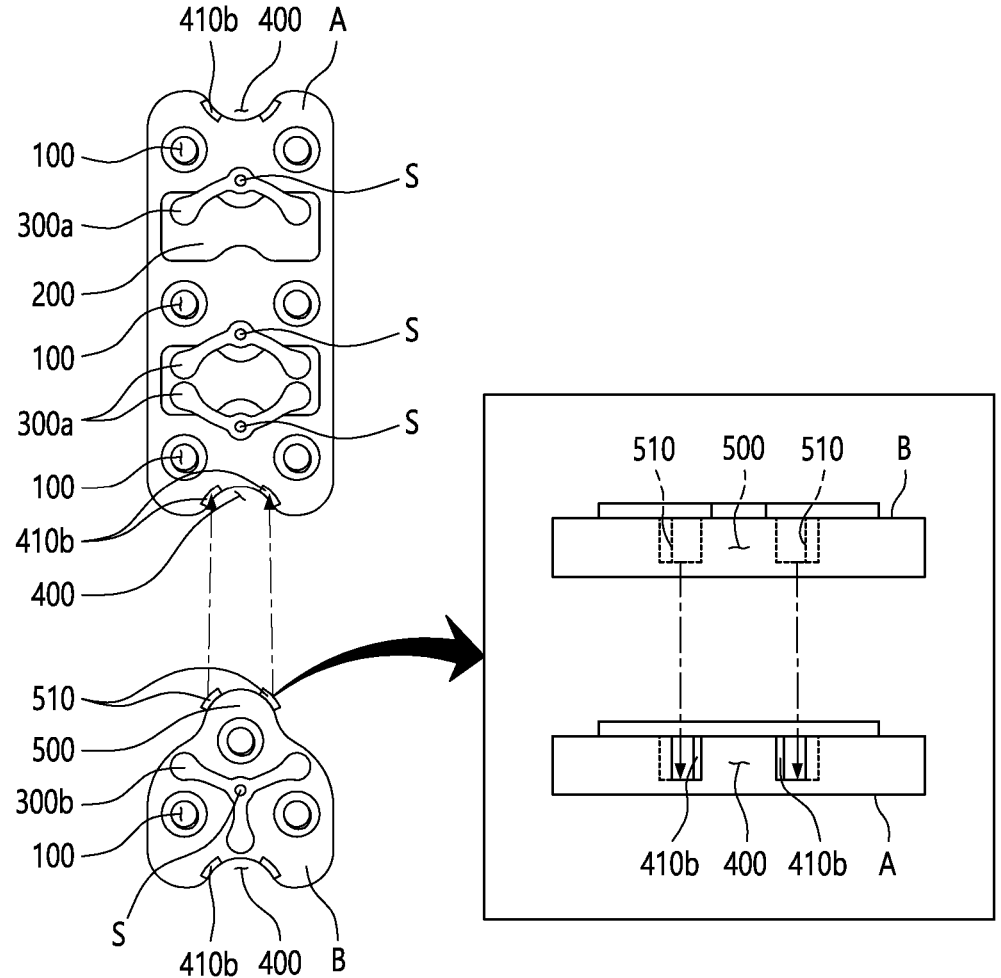

For example, on both sides of the inner circumferential surface of the fitting groove 400, as illustrated in FIGS. 6A and 6B, a coupling groove 410b which is bent in the vertical direction, that is, from the top to the bottom, may be formed.

At this time, the protrusion 500 fitted into the fitting groove 400 may have a coupling protrusion 510 protruding in the vertical direction at a position, which corresponds to the coupling groove 410b in the vertical direction, of the outer circumferential surface of the protrusion 500, so that the coupling protrusion 510 can be slidably inserted into the coupling groove 410b in the vertical direction, thereby allowing the main plate A to be slidably coupled to the subsidiary plate B in the vertical direction.

In this instance, the coupling protrusion 510 may have a tapered shape with a cross-sectional area increasing from the inside to the outside, and the coupling groove 410b into which the taper-shaped coupling protrusion 510 is inserted may also have a tapered shape corresponding to the tapered shape of the coupling protrusion 510.

Forming the coupling protrusion 510 and the coupling groove 410b in the tapered shape is to prevent horizontal separation of the coupling protrusion 510 from the coupling groove 410b due to a pulling force.

Moreover, as illustrated in FIGS. 6A and 6B, the coupling groove 410b is not limited to being formed on both sides of the inner circumferential surface of the fitting groove 400, and as occasion demands, may be formed at one side or more than three fitting grooves may be formed at regular intervals.

In other words, one or more coupling grooves 410b may be formed along the inner circumferential surface of the fitting groove 400.

Accordingly, it should be understood that the coupling protrusion 510, which is slidably inserted into the coupling groove 410b, is also not limited to being formed on both sides of the outer circumferential surface of the protrusion 500, and one or more coupling protrusions may be formed along the outer circumferential surface of the protrusion 500 in accordance with the number of coupling grooves 410b formed.

According to another embodiment of the present disclosure, the fitting groove 400 and the protrusion 500 can be engaged and coupled mutually complementally so that the coupling force between the main plate A having the fitting groove 400 and the subsidiary plate B having the protrusion 500 can be reinforced.

Figure 4A:
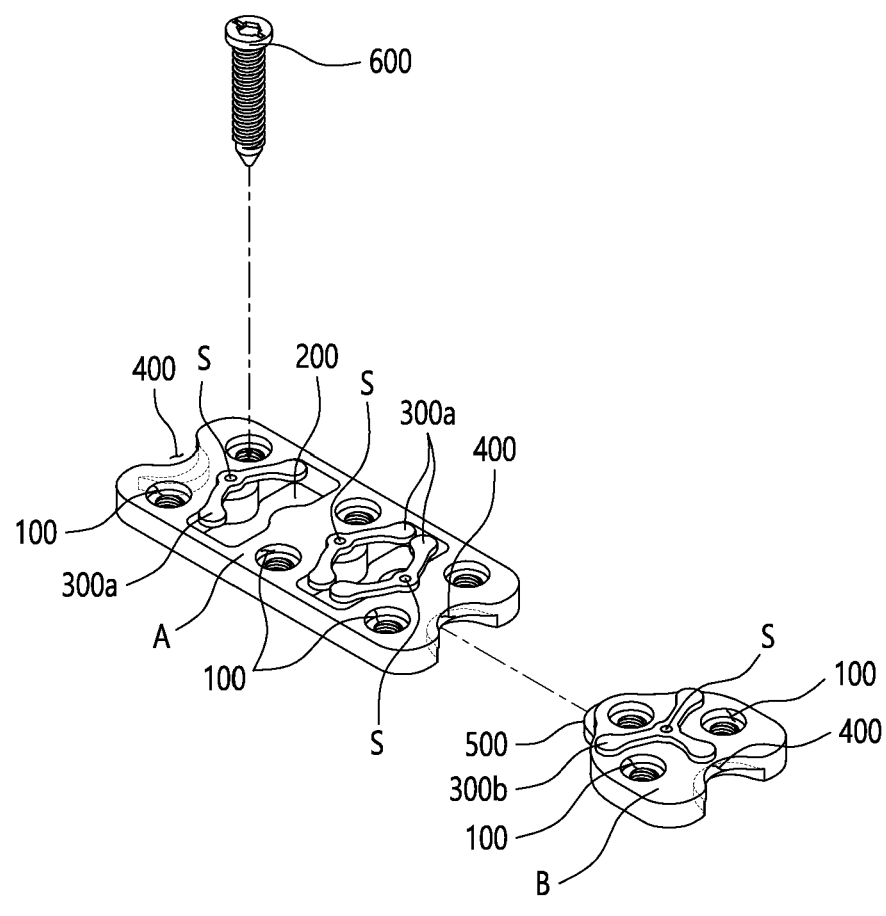
FIGS. 4A and 4B are illustrative views showing a coupling structure of a fitting groove and a protrusion in the cervical plate for easy reoperation according to the first embodiment of the present disclosure.
Figure 4B:
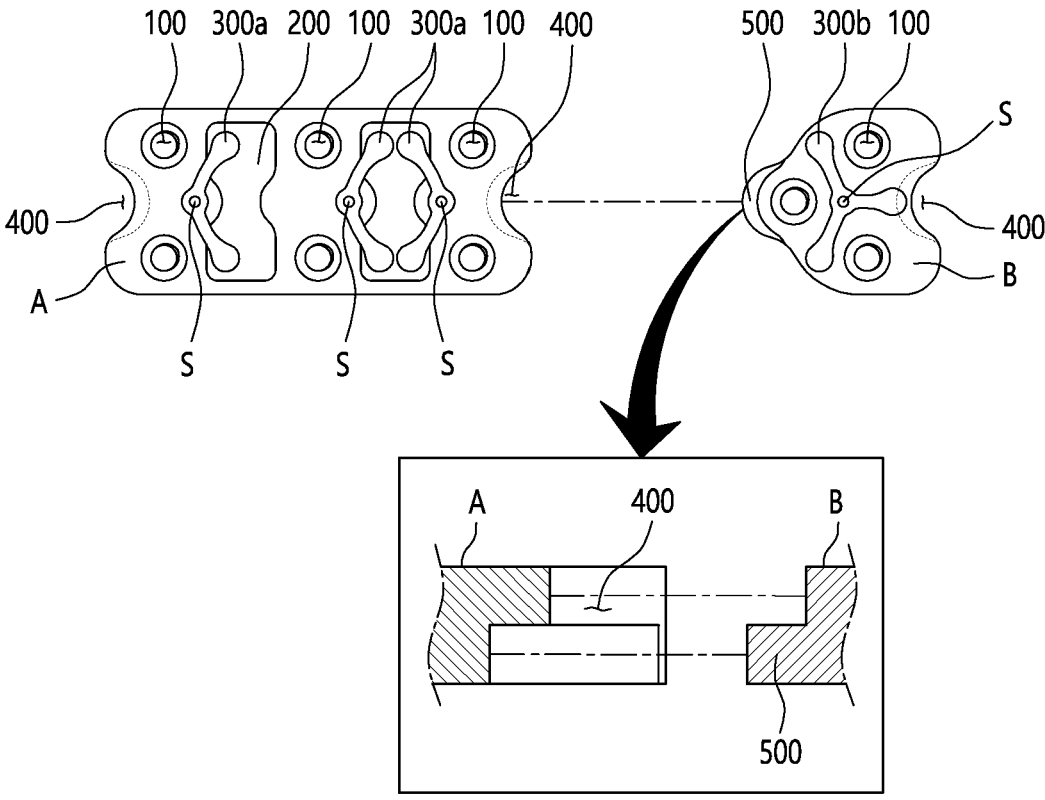

For example, as illustrated in FIGS. 4A and 4B, the fitting groove 400 and the protrusion 500, which have a structure that can be engaged and coupled mutually complementally, may be formed such that the lower portion of the fitting groove 400 is bent in the horizontal direction so that the upper portion and the lower portion can be differentiated and formed in multiple stages. Contrariwise, the protrusion 500 is formed in a structure that the upper portion of the fitting groove 400 is bent in the horizontal direction so that the upper portion and the lower portion can be differentiated and formed in multiple stages. Thus, when the fitting groove 400 and the protrusion 500 are closely engaged, they can complementarily engage with each other, thereby enhancing the coupling force between the main plate A and the subsidiary plate B.

In this instance, to be formed in multiple stages by engaging mutually complementarily means that the fitting groove 400, in which the lower portion is bent in the horizontal direction like a '⌈' shape, and the protrusion 500, in which the upper portion is bent in the horizontal direction like a '⌋' shape, closely engage with each other in a mutually complementary manner. The subsidiary plate B, which has the protrusion 500 formed in the shape in which the upper portion is bent in the horizontal direction, can be engaged and coupled with the main plate A, which has the fitting groove 400 formed in the shape in which the lower portion is bent in the horizontal direction, thereby preventing the subsidiary plate B from being indiscriminately lifted upwards.

At this time, although the fitting groove 400 and the protrusion 500 are illustrated as being formed in multiple stages in FIGS. 4A and 4B, it should be noted that it is just one embodiment of the multi-stage formation structure, and is not limited thereto. According to circumstances, the fitting groove 400 and the protrusion 500 can be formed in two to three stages, or in multiple stages, and can be engaged and coupled complementarily.

Figure 5A:
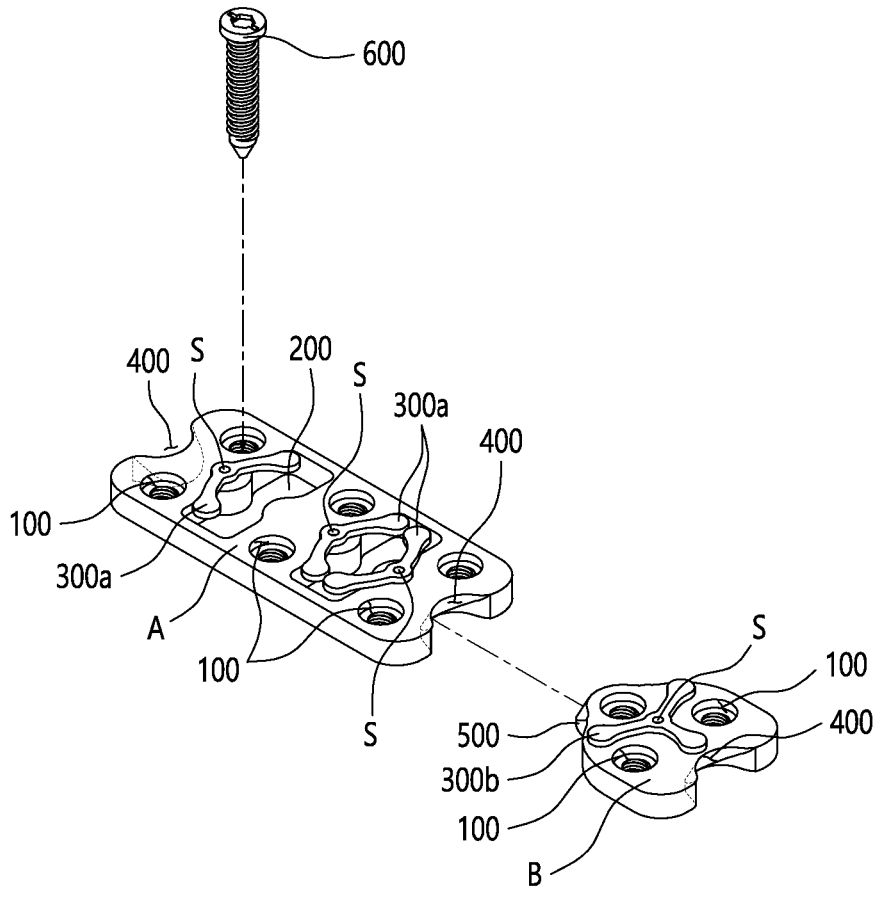
FIGS. 5A and 5B are illustrative views showing a coupling structure of a fitting groove and a protrusion in the cervical plate for easy reoperation according to a second embodiment of the present disclosure.
Figure 5B:
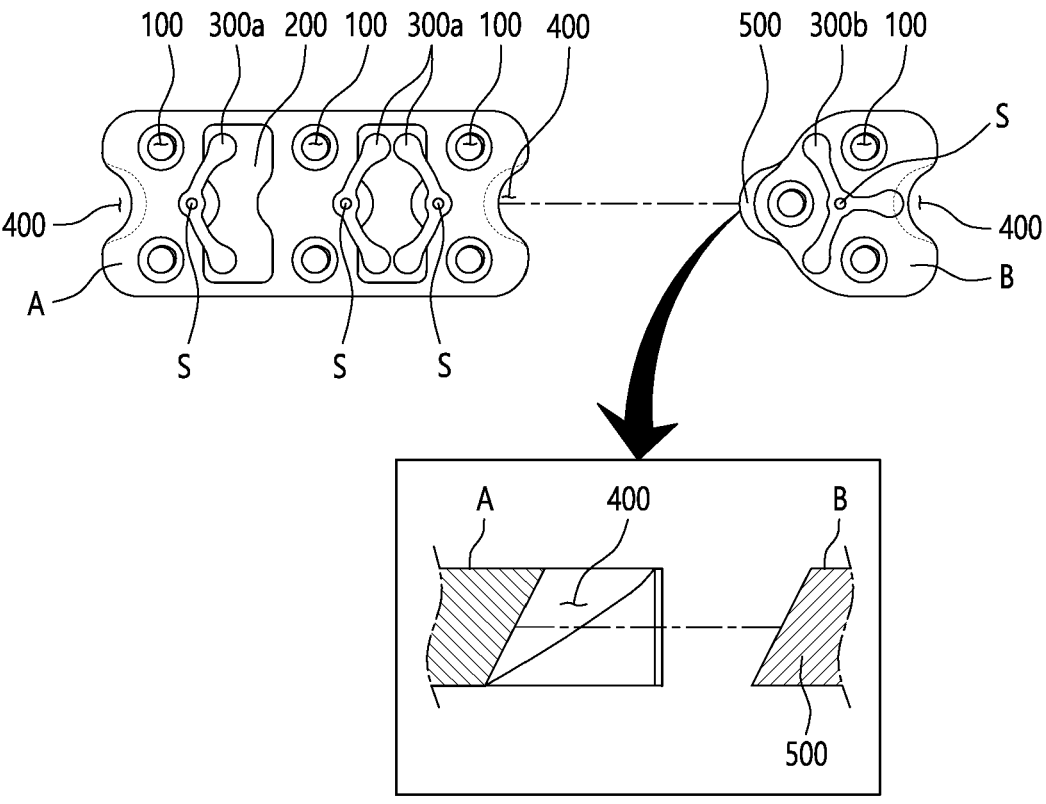

The shapes of the fitting groove 400 and the protrusion 500 are not limited to the multi-stage formation described in the above embodiment. As illustrated in FIGS. 5A and 5B, the lower portion of the fitting groove 400 and the upper portion of the protrusion 500 may be respectively bent in the horizontal direction, but may be formed in a tapered shape that tapers off in a diagonal direction to be engaged and coupled mutually complementarily.

In other words, the fitting groove 400 is formed in a tapered shape, in which the lower portion is bent in the horizontal direction, and tapers off from the upper portion to the lower portion. The protrusion 500, whose upper portion is bent in the horizontal direction, is formed in a tapered shape that tapers off from the lower portion to the upper portion, opposite to the bending direction of the fitting groove 400. So, the fitting groove 400 and the protrusion 500 can be engaged and coupled mutually complementarily.

In this instance, the inclined surfaces of the fitting groove 400 and the protrusion 500, which are formed in a tapered shape, are not limited to the formation of a single tapered inclined surface, as mentioned in the aforementioned embodiment of the multi-stage formation structure. According to circumstances, the fitting groove 400 and the protrusion 500 may have a structure with multiple tapered inclined surfaces formed continuously.

As described above, the cervical plate for easy reoperation according to the present disclosure allows for the additional installation of the subsidiary plate B without dismantling the already installed main plate A. Through the interaction between the fitting groove 400 and the protrusion 500, which are structured as mentioned above, the coupling force between the main plate A and the subsidiary plate B is reinforced, thereby ensuring a stable state even after the operation.

As described above, the preferred embodiments of the present disclosure have been described, and it is evident to those skilled in the art that the present disclosure can be embodied in other specific forms without departing from the spirit or scope of the present disclosure. Therefore, the described embodiments should be considered as illustrative and not restrictive, and thus, the present disclosure is not limited to the above descriptions but can be modified within the scope and equivalency range of the appended claims.

What is claimed is:

1. A cervical plate for reoperation, the cervical plate comprising:

a first plate having a rectangular panel shape, and configured to be installed using one or more screws on a surgical site of a vertebra to support and fix the vertebra; and a second plate having a panel shape and configured to be installed using the one or more screws on a reoperation site located in an adjacent area to the surgical site where the first plate is installed to support and fix the vertebra, the second plate including:

a plurality of fastening holes defined around a periphery of the second plate based on a center of the second plate, and a second cover unit rotatably coupled to an upper surface of the second plate via a second coupling shaft, and configured to cover a center point of each the plurality of fastening holes defined in the second plate, wherein the first plate and the second plate are continuously connected when installed, and the second plate is installed while maintaining an installed state of the first plate, wherein the first plate and the second plate respectively include the plurality of fastening holes, each the plurality of fastening holes having threads defined on an inner surface thereof to allow the one or more screws to penetrate in a screw manner and to be coupled to the vertebra, wherein the first plate includes a fitting groove defined on two opposite surfaces to which the second plate is connected, the fitting groove configured to allow one side of the second plate to fit into the first plate, wherein the fitting groove includes a coupling groove defined on an inner circumferential surface of the fitting groove and recessed inward in a direction that is vertically perpendicular to a longitudinal direction of the first plate, wherein the second plate includes a protrusion configured to fit into the fitting groove of the first plate, wherein the protrusion includes a coupling protrusion corresponding to the coupling groove and configured to be inserted and coupled into the coupling groove, wherein the coupling protrusion is disposed on an outer circumferential surface of the protrusion and protrudes outward in a direction vertically perpendicular to a longitudinal direction of the second plate, and wherein the coupling protrusion is slidably inserted into the coupling groove along the direction vertically perpendicular to the longitudinal direction of the first plate, allowing the first plate to be slidably coupled to the second plate in the direction vertically perpendicular to the longitudinal direction of the first plate.

2. The cervical plate according to claim 1, wherein the plurality of fastening holes formed in the first plate are formed in sets of two, and multiple sets of fastening holes are spaced at regular intervals in a length direction of the first plate.

3. The cervical plate according to claim 2, wherein the first plate further comprises: a first cover unit rotatably coupled to an upper surface of the first plate via a first coupling shaft, wherein the first cover unit selectively covers upper portions of one or more sets of the fastening holes formed in the first plate.

4. The cervical plate according to claim 3, wherein the first cover unit is formed in a 'A' shape extending in two directions from the first coupling shaft, and is provided in a same number as the sets of fastening holes formed in the first plate, and each of the first cover unit simultaneously opens or covers the upper portions of one set of the fastening holes formed in the first plate.

5. The cervical plate according to claim 1, wherein the second cover unit is:

coupled to the center of the second plate, formed to extend in three directions from the second coupling shaft, and configured to rotate and simultaneously open or cover upper portions of the plurality of fastening holes defined in the second plate.

6. The cervical plate according to claim 5, wherein the second cover unit has a 'Y' shape having three protruding ends respectively extending in the three directions about the second coupling shaft.

7. The cervical plate according to claim 1, wherein the first plate comprises at least one observation hole, which is formed to vertically penetrate the first plate, thereby allowing visual confirmation of a vertebral surface contacting with the first plate.

8. The cervical plate according to claim 1, wherein the protrusion has a tapered shape that narrows towards a distal end thereof to be inserted into the coupling groove.

9. The cervical plate according to claim 1, wherein the second cover unit has at least one protruding end having an extended bar and a hole cover at the end of the extended bar, and wherein the hole cover is configured to cover upper portions of the plurality of fastening holes defined in the second plate.

\* \* \* \* \*